United States Patent
Chang et al.

(10) Patent No.: US 12,252,694 B2
(45) Date of Patent: Mar. 18, 2025

(54) **GENOMIC EDITING VECTOR FOR *EUBACTERIUM CALLANDERI*, METHOD FOR EDITING GENOME OF *EUBACTERIUM CALLANDERI* USING THE SAME, AND TRANSGENIC *EUBACTERIUM CALLANDERI* STRAINS USING THE SAME**

(71) Applicant: GWANGJU INSTITUTE OF SCIENCE AND TECHNOLOGY, Gwangju (KR)

(72) Inventors: In Seop Chang, Gwangju (KR); Ji Yeon Kim, Gwangju (KR); Ji Yeong Jeong, Gwangju (KR); So Young Oh, Gwangju (KR); Jin Sung Jeon, Gwangju (KR)

(73) Assignee: GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 123 days.

(21) Appl. No.: 17/377,590

(22) Filed: Jul. 16, 2021

(65) Prior Publication Data
US 2022/0017910 A1  Jan. 20, 2022

(30) Foreign Application Priority Data
Jul. 17, 2020  (KR) ........................ 10-2020-0089015

(51) Int. Cl.
C12N 15/74 (2006.01)
C12N 9/22 (2006.01)
C12N 15/11 (2006.01)

(52) U.S. Cl.
CPC ............... *C12N 15/74* (2013.01); *C12N 9/22* (2013.01); *C12N 15/11* (2013.01); *C12N 2310/20* (2017.05); *C12N 2800/80* (2013.01)

(58) Field of Classification Search
CPC .......... C12N 15/74; C12N 15/00; C12N 9/22; C12N 15/11
See application file for complete search history.

(56) References Cited

U.S. PATENT DOCUMENTS

2019/0024123 A1* 1/2019 Berka ................. C12N 15/102

FOREIGN PATENT DOCUMENTS

KR  10-2017-0076822 A  7/2017
KR  20190024783 A  *  3/2019

OTHER PUBLICATIONS

Jeong et al., May 20, 2020, "Genetic engineering system for syngas-utilizing acetogen, Eubacterium limosum KIST612" Bioresource Technology Reports, 11 (2020), 100452 and Supplementary data (Year: 2020).*
Kim et al., 2023, "Genome-Based Reclassification of Strain KIST612, Previously Classified as Eubacterium limosum, into a New Strain of Eubacterium callanderi" Journal of Microbiology and Biotechnology, 33(8), p. 1084-1090 (Year: 2023).*
Shin et al., Aug. 2, 2019, "Genome Engineering of Eubacterium limosum Using Expanded Genetic Tools and the CRISPR-Cas9 System" ACS Synthetic Biology, 2019, 8, 2059-2068 and Supporting Information (Year: 2019).*
Addgene Plasmid #44250, pwtcas9, "Full sequences from Depositor (1)", first published Feb. 28, 2013, retrieved Apr. 12, 2024 (Year: 2013).*
Liu et al., Sep. 27, 2019, "Development and characterization of a CRISPR/Cas9n-based multiplex genome editing system for Bacillus subtilis" Biotechnology for Biofuels and Bioproducts, 12:197, p. 1-17 and Additional file 1 (Year: 2019).*

* cited by examiner

Primary Examiner — Jennifer Dunston
Assistant Examiner — Jenna L Persons
(74) Attorney, Agent, or Firm — Bridgeway IP Law Group, PLLC; Jihun Kim

(57) ABSTRACT

Proposed is a genomic editing vector for *Eubacterium callanderi* for the CRISPR/Cas9 system. The genomic editing vector for *Eubacterium callanderi* includes a DNA sequence encoding a guide RNA (gRNA) of a cleavage target gene; a DNA sequence encoding a Cas9 protein; a $P_{rbo}$ promoter that is operably linked to the DNA sequence encoding a Cas9 protein; a replication starting point derived from *E. coli*; a replication starting point for *Eubacterium callanderi*; and a marker for selecting transgenic strains. It is possible to provide a genomic editing vector for *Eubacterium callanderi* that can be applied to *Eubacterium callanderi* strains that are acetogen that is suitable for syngas biorefinery, a method for editing a genome of *Eubacterium callanderi* strains using the same, and transgenic *Eubacterium callanderi* strains using the same.

12 Claims, 13 Drawing Sheets

Specification includes a Sequence Listing.

P_rbo PROMOTER (5'->3')

ATTTTATAGGCATTTTCCGTTTAAAGTTTAAAAATTGTGGTATAATTAAT

FIG. 6 pMB1 ori (5'->3')

AGAAAGGCGGACAGGTATCCGGTAAGCGGCAGGGTCGGAACAGGAGAGCGCACGAGGGAGCTTCCAGGGGGAAAC

GCCTGGTATCTTTATAGTCCTGTCGGGTTTCGCCACCTCTGACTTGAGCGTCGATTTTTGTGATGCTCGTCAGGG

GGGCGGAGCCTATGGAAAAACGCCAGCAACGCGGCCTTTTTACGGTTCCTGGCCTTTTGCTGGCCTTTTGC

FIG. 7

```
pIP404 rep (5'->3')

TTATAAAAGCCCATTTTTTTTCATATACGTAATATGACGTTCTAATGTTTTTATTGGTACTTCTAACATTAGAGT
AATTTCTTTATTTTTAAAGCCTTTTTCTTTAAGGGCTTTTATTTTTTTCTTAATACATTTAATTCCTCTTTTTT
TGTTGCTTTTCCTTTAGCTTTTAATTGCTCTTGATAATTTTTTTTACCTCTAATATTTTCTCTTCTCTTATATTC
CTTTTTAGAAATTATTATTGTCATATATTTTGTTCTTCTTCTGTAATTTCTAATAACTCTATAAGAGTTTCATT
CTTATACTTATATTGCTTATTTTTATCTAAATAACATCTTTCAGCACTTCTAGTTGCTCTTATAACTTCTCTTTC
ACTTAAATGTTGTCTAAACATACTATTAAGTTCTAAAACATCATTTAATGCCTTCTCAATGTCTTCTGTAAAGCT
ACAAAGATAATATCTATATAAAAATAATATAAGCTCTCTGTGTCCTTTTAAATCATATTCTCTTAGTTCACAAAG
TTTTATTATGTCTTGTATTCTTCCATAATATAAACTTCTTTCTCTATAAATATAATTTATTTTGCTTGGTCTACC
CTTTTTCCTTTCATATGGTTTTAATTCAGGTAAAAATCCATTTTGTATTTCTCTTAAGTCATAAATATATTCGTA
CTCATCTAATATATTGACTACTGTTTTTGATTTAGAGTTTATACTTCCTGGAACTCTTAATATTCTCGTTGCATC
TAAGGCTTGTCTATCTGCTCCAAAGTATTTTAATTGATTATATAAATATTCTTGAACCGCTTTCCATAATGGTAA
TGCTTTACTAGGTACTGCATTTATTATCCATATTAAATACATTCCTCTTCCACTATCTATTACATAGTTTGGTAT
AGGAATACTTTGATTAAAATAATTCTTTTCTAAGTCCATTAATACCTGGTCTTTAGTTTTGCCAGTTTTATAATA
ATCCAAGTCTATAAACAGTGTATTTAACTCTTTTATATTTCTAATCGCCTACACGGCTTATAAAAGGTATTTAG
AGTTATATAGATATTTTCATCACTCATATCTAAATCTTTTAATTCAGCGTATTTATAGTGCCATTGGCTATATCC
TTTTTTATCTATAACGCTCCTGGTTATCCACCCTTTACTTCTACTATGAATATTATCTATATAGTTCTTTTTATT
CAGCTTTAATGCGTTTCTCAC
```

FIG. 8 sgRNA (5'->3')

TTGACAGCTAGCTCAGTCCTAGGTATAATCCCATCATCGCGGAATTTTCGTTTTAGAGCTAGAAATAGCAAGTTA

AAATAAGGCTAGTCCGTTATCAACTTGAAAAAGTGGCACCGAGTCGGTGCTTTT

FIG. 11

5' HOMOLOGY ARM (5'->3')

ACCTGGTGGATTTTGAGAGCACCCGGGAATACACCAATGTCTACTCCAACGATGGACACAATGTGGACAATGAAG

AGACCATGAAAAAGGGGCTGGCGGCTTCCACCGAGTACAATTTTATTCTGGCCACCCACTGTGAGCCGGAAACCG

AGACTGTGGAGCGGGACATCGCCCTTCTGCGTGAAACGCCTGGACACCTGCACGTGTGCCATATCAGCAAAAAAG

ATACCCTGGAAGCCATCAAGGCCGCCAAAGCAGAGGGTCTGGACATTACCTGTGAGGTCACCCCGCACCATCTGT

ACGCCTCTGCCATGGAGTATAAGGTACACCCGCCGTTCAGAAGCTACCCGGACCGCCGGGCGCTCATCGAGGGCG

CCCGGGACGGCAGCATTGACATCTGCGGCACCGACCACGCCCCACACAGCGACGAGGACAAGCTGAAAGGCGCGC

CGGGGATCAATAATTTTGAGACCGCCTTTGCCATGTACTACACTGTTTTTGAGGGAGCGGGTATTTCTGTGGAAC

GCCTGAGTCAGATGCTGAGCGAGGCGCCGGCTGAGCGCATGGGGATAAAGGCCGGCCTGGTCAAGGAACGCTACG

CCGGAGACCTGGTTTTAGTGGATCTGGACGCTGAGGAACGGGTAGACCCCAGGACCTTTATCTCAAAAAGCCACA

ACACCCCCTTTGGCAGGGAACTGCTCAAGGGCAAGGTGCTCATGACATTTAAAGGAGGAGAGATCGCATATGATA

ATGGATCGCTTGTATAACGAAGCATTAAAAAGCCCCGTCTGTGTGGGCCTGGATACAAAAATTGACTTTCTGCCC

CAGTACCTGAAGGATAAGGACTGGTCAGCCGG

FIG. 12

3' HOMOLOGY ARM (5'->3')

ATCAGAAGGCAGAGACCCCCTGTGAGACCGAGGGCTTTGAAGCCCTGATCCGTGAAAAAACACTGGCCATGAAGG
AGGACATTTTAAAGTGGCTTTAATTTTAGATAACCAGTTTGTGGCCGAGGGCATTTACAAAATGGACGTGGCCTA
CGACGGTGAAGTGGGCGTCGGCCAGTTTTTCATGCTGAGAGCCTGGGATAAGGACCCGCTGCTGTCACGGCCCAT
CTCCGTCCATAATTACGAAAACGGTGTGCTCACCTTCCTGTATCAGATTGTAGGCAAGGGCACCCAGCTTTTGTC
AAAACTGGAAAAGGACGACACTGTGGAATTACAGGGCCCGTACGGCAAGGGCTTCCCGGATGTGGACGCCGACCT
GGTGGTGGTGGGCGGCGGCATTGGTGTCGCGCCCTGTACTATGTGTGCCGCGACTTCAAGAAAAAACACCCGGA
CCGCAGCCTGCGTGTTTACCTGGGCTACCGCGACACTGCCTACTGTGTGGAGGAATTTGACGCAGTGGCCGATGA
AGTGGTCGTGGATATCGGCGGCATCATCACCCACCGGGTAGAAGCCCGTTCCGGCGAGGTATTCTTTACCTGCGG
CCCGGAAATCATGATGAAGAGCCTGTGTGACATTGTCCCGGCCGAAAACCCGGTTTACGTGTCGCTGGAGGCGCA
TATGGCCTGCGGCATCGGCGCCTGTCTGGGCTGCACCTGCGAGACCAGTGAAGGCAATAAGAAGGTCTGTAAGGA
CGGGCCAGTGTTTACCAGAGAGGTGGCAGCCCTATGA

FIG. 13

SEQUENCE LISTING

<160> NUMBER OF SEQ ID NOS: 16

<210> SEQ ID NO 1
<211> LENGTH: 4107

```
<212> TYPE: DNA
<213> ORGANISM: Strelitzia nicolai

<400> SEQUENCE: 1
```

| | | | | | |
|---|---|---|---|---|---|
| atggataaga | aatactcaat | aggcttagat | atcggcacaa | atagcgtcgg | atgggcggtg | 60 |
| atcactgatg | aatataaggt | tccgtctaaa | aagttcaagg | ttctgggaaa | tacagaccgc | 120 |
| cacagtatca | aaaaaaatct | tatagggggct | cttttatttg | acagtggaga | gacagcggaa | 180 |
| gcgactcgtc | tcaaacggac | agctcgtaga | aggtatacac | gtcggaagaa | tcgtatttgt | 240 |
| tatctacagg | agattttttc | aaatgagatg | gcgaaagtag | atgatagttt | ctttcatcga | 300 |
| cttgaagagt | cttttttggt | ggaagaagac | aagaagcatg | aacgtcatcc | tattttgga | 360 |
| aatatagtag | atgaagttgc | ttatcatgag | aaatatccaa | ctatctatca | tctgcgaaaa | 420 |
| aaattggtag | attctactga | taaagcggat | ttgcgcttaa | tctatttggc | cttagcgcat | 480 |
| atgattaagt | tcgtggtca | ttttttgatt | gagggagatt | taaatcctga | taatagtgat | 540 |
| gtggacaaac | tatttatcca | gttggtacaa | acctacaatc | aattatttga | agaaaaccct | 600 |
| attaacgcaa | gtggagtaga | tgctaaagcg | attcttctg | cacgattgag | taaatcaaga | 660 |
| cgattagaaa | atctcattgc | tcagctcccc | ggtgagaaga | aaaatggctt | atttgggaat | 720 |
| ctcattgctt | tgtcattggg | tttgaccct | aatttaaat | caaattttga | tttggcagaa | 780 |
| gatgctaaat | tacagctttc | aaaagatact | tacgatgatg | atttagataa | tttattggcg | 840 |
| caaattggag | atcaatatgc | tgatttgttt | ttggcagcta | agaatttatc | agatgctatt | 900 |
| ttactttcag | atatcctaag | agtaaatact | gaaataacta | aggctcccct | atcagcttca | 960 |
| atgattaaac | gctacgatga | acatcatcaa | gacttgactc | ttttaaaagc | tttagttcga | 1020 |
| caacaacttc | cagaaaagta | taagaaaatc | ttttttgatc | aatcaaaaaa | cggatatgca | 1080 |
| ggttatattg | atgggggagc | tagccaagaa | gaattttata | aatttatcaa | accaatttta | 1140 |
| gaaaaaatgg | atggtactga | ggaattattg | gtgaaactaa | atcgtgaaga | tttgctgcgc | 1200 |
| aagcaacgga | cctttgacaa | cggctctatt | ccccatcaaa | ttcacttggg | tgagctgcat | 1260 |
| gctattttga | aagacaaga | agacttttat | ccatttttaa | aagacaatcg | tgagaagatt | 1320 |
| gaaaaaatct | tgactttcg | aattccttat | tatgttggtc | cattggcgcg | tggcaatagt | 1380 |
| cgttttgcat | ggatgactcg | gaagtctgaa | gaaacaatta | ccccatggaa | ttttgaagaa | 1440 |
| gttgtcgata | aaggtgcttc | agctcaatca | tttattgaac | gcatgacaaa | ctttgataaa | 1500 |
| aatcttccaa | atgaaaaagt | actaccaaaa | catagtttgc | tttatgagta | ttttacggtt | 1560 |
| tataacgaat | tgacaaaggt | caaatatgtt | actgaaggaa | tgcgaaaacc | agcatttctt | 1620 |
| tcaggtgaac | agaagaaagc | cattgttgat | ttactcttca | aaacaaatcg | aaaagtaacc | 1680 |
| gttaagcaat | taaagaaga | ttatttcaaa | aaaatagaat | gttttgatag | tgttgaaatt | 1740 |
| tcaggagttg | aagatagatt | taatgcttca | ttaggtacct | accatgattt | gctaaaaatt | 1800 |
| attaaagata | aagattttt | ggataatgaa | gaaatgaag | atatcttaga | ggatattgtt | 1860 |
| ttaacattga | ccttatttga | agatagggag | atgattgagg | aaagacttaa | aacatatgct | 1920 |
| cacctctttg | atgataaggt | gatgaaacag | cttaaacgtc | gccgttatac | tggttgggga | 1980 |
| cgtttgtctc | gaaaattgat | taatggtatt | agggataagc | aatctggcaa | aacaatatta | 2040 |
| gattttttga | aatcagatgg | ttttgccaat | cgcaatttta | tgcagctgat | ccatgatgat | 2100 |
| agtttgacat | ttaagaaga | cattcaaaaa | gcacaagtgt | ctggacaagg | cgatagttta | 2160 |
| catgaacata | ttgcaaattt | agctggtagc | cctgctatta | aaaaggtat | tttacagact | 2220 |

| | |
|---|---|
| gtaaaagttg ttgatgaatt ggtcaaagta atggggcggc ataagccaga aaatatcgtt | 2280 |
| attgaaatgg cacgtgaaaa tcagacaact caaaagggcc agaaaaattc gcgagagcgt | 2340 |
| atgaaacgaa tcgaagaagg tatcaaagaa ttaggaagtc agattcttaa agagcatcct | 2400 |
| gttgaaaata ctcaattgca aaatgaaaag ctctatctct attatctcca aaatggaaga | 2460 |
| gacatgtatg tggaccaaga attagatatt aatcgtttaa gtgattatga tgtcgatcac | 2520 |
| attgttccac aaagtttcct taaagacgat tcaatagaca ataaggtctt aacgcgttct | 2580 |
| gataaaaatc gtggtaaatc ggataacgtt ccaagtgaag aagtagtcaa aaagatgaaa | 2640 |
| aactattgga gacaacttct aaacgccaag ttaatcactc aacgtaagtt tgataattta | 2700 |
| acgaaagctg aacgtggagg tttgagtgaa cttgataaag ctggttttat caaacgccaa | 2760 |
| ttggttgaaa ctcgccaaat cactaagcat gtggcacaaa ttttggatag tcgcatgaat | 2820 |
| actaaatacg atgaaaatga taaacttatt cgagaggtta agtgattac cttaaaatct | 2880 |
| aaattagttt ctgacttccg aaaagatttc caattctata agtacgtga gattaacaat | 2940 |
| taccatcatg cccatgatgc gtatctaaat gccgtcgttg gaactgcttt gattaagaaa | 3000 |
| tatccaaaac ttgaatcgga gtttgtctat ggtgattata agtttatga tgttcgtaaa | 3060 |
| atgattgcta agtctgagca agaaataggc aaagcaaccg caaatatttt ctttactct | 3120 |
| aatatcatga acttcttcaa aacagaaatt acacttgcaa atggagagat tcgcaaacgc | 3180 |
| cctctaatcg aaactaatgg ggaaactgga gaaattgtct gggataaagg gcgagatttt | 3240 |
| gccacagtgc gcaaagtatt gtccatgccc caagtcaata ttgtcaagaa aacagaagta | 3300 |
| cagacaggcg gattctccaa ggagtcaatt ttaccaaaaa gaaattcgga caagcttatt | 3360 |
| gctcgtaaaa aagactggga tccaaaaaaa tatggtggtt ttgatagtcc aacggtagct | 3420 |
| tattcagtcc tagtggttgc taaggtggaa aagggaaat cgaagaagtt aaaatccgtt | 3480 |
| aaagagttac tagggatcac aattatggaa agaagttcct ttgaaaaaaa tccgattgac | 3540 |
| ttttagaag ctaaaggata taggaagtt aaaaaagact taatcattaa actacctaaa | 3600 |
| tatagtcttt ttgagttaga aaacggtcgt aaacggatgc tggctagtgc cggagaatta | 3660 |
| caaaaaggaa atgagctggc tctgccaagc aaatatgtga ttttttata tttagctagt | 3720 |
| cattatgaaa agttgaaggg tagtccagaa gataacgaac aaaaacaatt gtttgtggag | 3780 |
| cagcataagc attatttaga tgagattatt gagcaaatca gtgaattttc taagcgtgtt | 3840 |
| attttagcag atgccaattt agataaagtt cttagtgcat ataacaaaca tagagacaaa | 3900 |
| ccaatacgtg aacaagcaga aaatattatt catttattta cgttgacgaa tcttggagct | 3960 |
| cccgctgctt ttaaatattt tgatacaaca attgatcgta acgatatac gtctacaaaa | 4020 |
| gaagttttag atgccactct tatccatcaa tccatcactg gtctttatga aacacgcatt | 4080 |
| gatttgagtc agctaggagg tgactga | 4107 |

<210> SEQ ID NO 2
<211> LENGTH: 4107
<212> TYPE: DNA
<213> ORGANISM: Artificial Sequence
<220> FEATURE:
<223> OTHER INFORMATION: Cas9 nickase gene in which the tenth amino acid
    is substituted with alanine for Cas9 protein derived from
    Streptococcus

<400> SEQUENCE: 2

| | |
|---|---|
| atggataaga aatactcaat aggcttagct atcggcacaa atagcgtcgg atgggcggtg | 60 |
| atcactgatg aatataaggt tccgtctaaa aagttcaagg ttctgggaaa tacagaccgc | 120 |

```
cacagtatca aaaaaaatct tatagggget cttttatttg acagtggaga gacagcggaa    180
gcgactcgtc tcaaacggac agctcgtaga aggtatacac gtcggaagaa tcgtatttgt    240
tatctacagg agattttttc aaatgagatg gcgaaagtag atgatagttt ctttcatcga    300
cttgaagagt ctttttggt ggaagaagac aagaagcatg aacgtcatcc tatttttgga    360
aatatagtag atgaagttgc ttatcatgag aaatatccaa ctatctatca tctgcgaaaa    420
aaattggtag attctactga taaagcggat ttgcgcttaa tctatttggc cttagcgcat    480
atgattaagt ttcgtggtca tttttttgatt gagggagatt taaatcctga taatagtgat    540
gtggacaaac tatttatcca gttggtacaa acctacaatc aattatttga agaaaaccct    600
attaacgcaa gtggagtaga tgctaaagcg attctttctg cacgattgag taaatcaaga    660
cgattagaaa atctcattgc tcagctcccc ggtgagaaga aaaatggctt atttgggaat    720
ctcattgctt tgtcattggg tttgaccccct aattttaaat caaattttga tttggcagaa    780
gatgctaaat tacagctttc aaaagatact tacgatgatg atttagataa tttattggcg    840
caaattggag atcaatatgc tgatttgttt ttggcagcta agaatttatc agatgctatt    900
ttactttcag atatcctaag agtaaatact gaaataacta aggctcccct atcagcttca    960
atgattaaac gctacgatga acatcatcaa gacttgactc ttttaaaagc tttagttcga   1020
caacaacttc cagaaaagta taagaaaatc ttttttgatc aatcaaaaaa cggatatgca   1080
ggttatattg atgggggagc tagccaagaa gaattttata aatttatcaa accaatttta   1140
gaaaaaatgg atggtactga ggaattattg gtgaaactaa atcgtgaaga tttgctgcgc   1200
aagcaacgga ccttttgacaa cggctctatt cccccatcaaa ttcacttggg tgagctgcat   1260
gctattttga aagacaaga agactttat ccatttttaa aagacaatcg tgagaagatt   1320
gaaaaaatct tgactttcg aattccttat tatgttggtc cattggcgcg tggcaatagt   1380
cgttttgcat ggatgactcg gaagtctgaa gaaacaatta ccccatgaa ttttgaagaa   1440 gttgtcgata aggtgcttc agctcaatca tttattgaac gcatgacaaa cttttgataaa   1500 aatcttccaa atgaaaaagt actaccaaaa catagtttgc tttatgagta ttttacggtt   1560
tataacgaat tgacaaaggt caaatatgtt actgaaggaa tgcgaaaacc agcatttctt   1620
tcaggtgaac agaagaaagc cattgttgat ttactcttca aaacaaatcg aaaagtaacc   1680
gttaagcaat taaagaaga ttatttcaaa aaaatagaat gttttgatag tgttgaaatt   1740
tcaggagttg aagatagatt taatgcttca ttaggtacct accatgattt gctaaaaatt   1800
attaaagata aagattttt ggataatgaa gaaaatgaag atatcttaga ggatattgtt   1860
ttaacattga ccttatttga agataggag atgattgagg aaagacttaa aacatatgct   1920
caccctcttg atgataaggt gatgaaacag cttaaacgtc gccgttatac tggttgggga   1980
cgtttgtctc gaaaattgat taatggtatt agggataagc aatctggcaa aacaatatta   2040
gattttttga aatcagatgg tttttgccaat cgcaatttta tgcagctgat ccatgatgat   2100
agtttgacat ttaaagaaga cattcaaaaaa gcacaagtgt ctggacaagg cgatagttta   2160
catgaacata ttgcaaattt agctggtagc cctgctatta aaaaggtat tttacagact   2220 gtaaaagttg ttgatgaatt ggtcaaagta atggggcggc ataagccaga aaatatcgtt   2280
attgaaatgg cacgtgaaaa tcagacaact caaaagggcc agaaaaattc gcgagagcgt   2340
atgaaacgaa tcgaagaagg tatcaaagaa ttaggaagtc agattcttaa agagcatcct   2400
gttgaaaata ctcaattgca aaatgaaaag ctctatctct attatctcca aaatggaaga   2460
```

```
gacatgtatg tggaccaaga attagatatt aatcgtttaa gtgattatga tgtcgatcac    2520
attgttccac aaagtttcct taaagacgat tcaatagaca ataaggtctt aacgcgttct    2580
gataaaaatc gtggtaaatc ggataacgtt ccaagtgaag aagtagtcaa aaagatgaaa    2640
aactattgga gacaacttct aaacgccaag ttaatcactc aacgtaagtt tgataattta    2700
acgaaagctg aacgtggagg tttgagtgaa cttgataaag ctggttttat caaacgccaa    2760
ttggttgaaa ctcgccaaat cactaagcat gtggcacaaa ttttggatag tcgcatgaat    2820
actaaatacg atgaaaatga taaacttatt cgagaggtta aagtgattac cttaaaatct    2880
aaattagttt ctgacttccg aaaagatttc caattctata aagtacgtga gattaacaat    2940
taccatcatg cccatgatgc gtatctaaat gccgtcgttg gaactgcttt gattaagaaa    3000
tatccaaaac ttgaatcgga gtttgtctat ggtgattata agtttatga tgttcgtaaa     3060 atgattgcta agtctgagca agaaataggc aaagcaaccg caaatatttt ctttactct    3120 aatatcatga acttcttcaa aacagaaatt acacttgcaa atggagagat tcgcaaacgc    3180
cctctaatcg aaactaatgg ggaaactgga gaaattgtct gggataaagg gcgagatttt    3240
gccacagtgc gcaaagtatt gtccatgccc caagtcaata ttgtcaagaa aacagaagta    3300
cagacaggcg gattctccaa ggagtcaatt ttaccaaaaa gaaattcgga caagcttatt    3360
gctcgtaaaa aagactggga tccaaaaaaa tatggtggtt tgatagtcc aacggtagct     3420 tattcagtcc tagtggttgc taaggtggaa aaagggaaat cgaagaagtt aaaatccgtt    3480
aaagagttac tagggatcac aattatggaa agaagttcct ttgaaaaaaa tccgattgac    3540
tttttagaag ctaaaggata taaggaagtt aaaaaagact taatcattaa actacctaaa    3600
tatagtcttt ttgagttaga aaacggtcgt aaacggatgc tggctagtgc cggagaatta    3660
caaaaaggaa atgagctggc tctgccaagc aaatatgtga atttttttata tttagctagt    3720 cattatgaaa agttgaaggg tagtccagaa gataacgaac aaaaacaatt gtttgtggag    3780
cagcataagc attatttaga tgagattatt gagcaaatca gtgaatttc taagcgtgtt     3840 attttagcag atgccaattt agataaagtt cttagtgcat ataacaaaca tagagacaaa    3900
ccaatacgtg aacaagcaga aaatattatt catttattta cgttgacgaa tcttggagct    3960
cccgctgctt ttaaatattt tgatacaaca attgatcgta acgatatac gtctacaaaa     4020 gaagttttag atgccactct tatccatcaa tccatcactg gtctttatga aacacgcatt    4080
gatttgagtc agctaggagg tgactga                                       4107

<210> SEQ ID NO 3
<211> LENGTH: 50
<212> TYPE: DNA
<213> ORGANISM: Eubacterium limosum

<400> SEQUENCE: 3
attttatagg cattttccgt ttaaagttta aaaattgtgg tataattaat                50

<210> SEQ ID NO 4
<211> LENGTH: 221
<212> TYPE: DNA
<213> ORGANISM: Escherichia coli

<400> SEQUENCE: 4
agaaaggcgg acaggtatcc ggtaagcggc agggtcggaa caggagagcg cacgagggag     60
cttccagggg gaaacgcctg gtatctttat agtcctgtcg ggtttcgcca cctctgactt    120
gagcgtcgat ttttgtgatg ctcgtcaggg gggcggagcc tatggaaaaa cgccagcaac    180
```

```
gcggccttttt tacggttcct ggccttttgc tggccttttg c            221
```

<210> SEQ ID NO 5
<211> LENGTH: 1221
<212> TYPE: DNA
<213> ORGANISM: Artificial Sequence
<220> FEATURE:
<223> OTHER INFORMATION: pIP404 replication origin from pJIR750 vector

<400> SEQUENCE: 5

```
ttataaaagc ccattttttt tcatatacgt aatatgacgt tctaatgttt ttattggtac     60
ttctaacatt agagtaattt ctttattttt aaagcccttt tctttaaggg cttttatttt    120
ttttcttaat acatttaatt cctctttttt tgttgctttt cctttagctt taattgctc    180
ttgataattt tttttacctc taatattttc tcttctctta tattcctttt tagaaattat    240
tattgtcata tattttgtt cttcttctgt aatttctaat aactctataa gagtttcatt    300
cttatactta tattgcttat ttttatctaa ataacatctt tcagcacttc tagttgctct    360
tataacttct ctttcactta aatgttgtct aaacatacta ttaagttcta aaacatcatt    420
taatgccttc tcaatgtctt ctgtaaagct acaaagataa tatctatata aaataatat    480
aagctctctg tgtcctttta aatcatattc tcttagttca caaagttta ttatgtcttg    540
tattcttcca taatataaac ttctttctct ataaatataa tttatttgc ttggtctacc    600
cttttccctt tcatatggtt ttaattcagg taaaatcca ttttgtattt ctcttaagtc    660
ataaatatat tcgtactcat ctaatatatt gactactgtt tttgatttag agtttatact    720
tcctggaact cttaatattc tcgttgcatc taaggcttgt ctatctgctc caaagtattt    780
taattgatta tataaatatt cttgaaccgc tttccataat ggtaatgctt tactaggtac    840
tgcatttatt atccatatta aatacattcc tcttccacta tctattacat agtttggtat    900
aggaatactt tgattaaat aattcttttc taagtccatt aatacctggt ctttagtttt    960
gccagtttta taataatcca agtctataaa cagtgtattt aactctttta tattttctaa  1020
tcgcctacac ggcttataaa aggtatttag agttatatag atattttcat cactcatatc  1080
taaatctttt aattcagcgt atttatagtg ccattggcta tatccttttt tatctataac  1140
gctcctggtt atccacccctt tacttctact atgaatatta tctatatagt tcttttttatt  1200
cagctttaat gcgtttctca c                                            1221
```

<210> SEQ ID NO 6
<211> LENGTH: 37
<212> TYPE: DNA
<213> ORGANISM: Artificial Sequence
<220> FEATURE:
<223> OTHER INFORMATION: forward primer for back bone vector

<400> SEQUENCE: 6

```
gttacatcgg gttacatcga actggatctc aacagcg              37
```

<210> SEQ ID NO 7
<211> LENGTH: 30
<212> TYPE: DNA
<213> ORGANISM: Artificial Sequence
<220> FEATURE:
<223> OTHER INFORMATION: reverse primer for back bone vector

<400> SEQUENCE: 7

```
gactagtcag aatcagggga taacgcagga              30
```

<210> SEQ ID NO 8
<211> LENGTH: 74
<212> TYPE: DNA
<213> ORGANISM: Artificial Sequence
<220> FEATURE:
<223> OTHER INFORMATION: forward primer for Prbo promoter

<400> SEQUENCE: 8
ctcacatgtt ctttcctgcg ttatcccctg attctgacta gtctgcacca tcaatgacat        60
cacacagcat aacg                                                          74

<210> SEQ ID NO 9
<211> LENGTH: 70
<212> TYPE: DNA
<213> ORGANISM: Artificial Sequence
<220> FEATURE:
<223> OTHER INFORMATION: reverse primer for Prbo promoter

<400> SEQUENCE: 9
agcctattga gtatttctta tccataataa agacctccta tagtccaaat ataattttga        60
gcagtccgtg                                                               70

<210> SEQ ID NO 10
<211> LENGTH: 91
<212> TYPE: DNA
<213> ORGANISM: Artificial Sequence
<220> FEATURE:
<223> OTHER INFORMATION: forward primer for Cas9

<400> SEQUENCE: 10
cacggactgc tcaaaattat atttggacta taggaggtct ttattatgga taagaaatac        60
tcaataggct agatatcgg cacaaatagc g                                        91

<210> SEQ ID NO 11
<211> LENGTH: 74
<212> TYPE: DNA
<213> ORGANISM: Artificial Sequence
<220> FEATURE:
<223> OTHER INFORMATION: reverse primer for Cas9

<400> SEQUENCE: 11
atcttaccgc tgttgagatc cagttcgatg taacccgatg taaccccact atttgtctca        60
gctagacttc agtc                                                          74

<210> SEQ ID NO 12
<211> LENGTH: 90
<212> TYPE: DNA
<213> ORGANISM: Artificial Sequence
<220> FEATURE:
<223> OTHER INFORMATION: forward primer for Cas9n

<400> SEQUENCE: 12
cacggactgc tcaaaattat atttggacta taggaggtct ttattatgga taagaaatac        60
tcaataggct agctatcgg cacaaatagc                                          90

<210> SEQ ID NO 13
<211> LENGTH: 66
<212> TYPE: DNA
<213> ORGANISM: Artificial Sequence
<220> FEATURE:
<223> OTHER INFORMATION: reverse primer for Cas9n

<400> SEQUENCE: 13

```
atcttaccgc tgttgagatc cagttcgatg taacccgatg taaccccgat taagttgggt    60
aacgcc                                                               66
```

<210> SEQ ID NO 14
<211> LENGTH: 129
<212> TYPE: DNA
<213> ORGANISM: Artificial Sequence
<220> FEATURE:
<223> OTHER INFORMATION: DNA encoding Guide RNA for pyrF gene in
      Eubacterium callanderi

<400> SEQUENCE: 14

```
ttgacagcta gctcagtcct aggtataatc ccatcatcgc ggaattttcg ttttagagct    60
agaaatagca agttaaaata aggctagtcc gttatcaact gaaaaagtg gcaccgagtc    120 ggtgctttt                                                           129
```

<210> SEQ ID NO 15
<211> LENGTH: 857
<212> TYPE: DNA
<213> ORGANISM: Artificial Sequence
<220> FEATURE:
<223> OTHER INFORMATION: Homology arm for pyrF gene editing in
      Eubacterium callanderi

<400> SEQUENCE: 15

```
acctggtgga ttttgagagc acccgggaat acaccaatgt ctactccaac gatggacaca    60
atgtggacaa tgaagagacc atgaaaaagg ggctggcggc ttccaccgag tacaattta    120 ttctggccac ccactgtgag ccggaaaccg agactgtgga gcgggacatc gcccttctgc   180
gtgaaacgcc tggacacctg cacgtgtgcc atatcagcaa aaagatacc ctggaagcca   240 tcaaggccgc caaagcagag ggtctggaca ttacctgtga ggtcaccccg caccatctgt   300
acgcctctgc catggagtat aaggtacacc cgccgttcag aagctacccg gaccgccggg   360
cgctcatcga gggcgcccgg gacggcagca ttgacatctg cggcaccgac cacgccccac   420
acagcgacga ggacaagctg aaaggcgcgc cggggatcaa taattttgag accgcctttg   480
ccatgtacta cactgttttt gagggagcgg gtatttctgt ggaacgcctg agtcagatgc   540
tgagcgaggc gccggctgag cgcatgggga taaaggccgg cctggtcaag aacgctacg    600 ccggagacct ggttttagtg gatctggacg ctgaggaacg ggtagacccc aggacccttta   660 tctcaaaaag ccacaacacc cccttttggca gggaactgct caagggcaag gtgctcatga   720
catttaaagg aggagagatc gcatatgata atggatcgct tgtataacga agcattaaaa   780
agccccgtct gtgtgggcct ggatacaaaa attgactttc tgccccagta cctgaaggat   840
aaggactggt cagccgg                                                  857
```

<210> SEQ ID NO 16
<211> LENGTH: 787
<212> TYPE: DNA
<213> ORGANISM: Artificial Sequence
<220> FEATURE:
<223> OTHER INFORMATION: Homology arm for pyrF gene editing in
      Eubacterium callanderi

<400> SEQUENCE: 16

```
atcagaaggc agagaccccc tgtgagaccg agggctttga agccctgatc cgtgaaaaaa    60
cactggccat gaaggaggac atttaaagt ggctttaatt ttagataacc agtttgtggc    120
cgagggcatt tacaaaatgg acgtggccta cgacggtgaa gtgggcgtcg gccagttttt   180
```

-continued

```
catgctgaga gcctgggata aggacccgct gctgtcacgg cccatctccg tccataatta    240
cgaaaacggt gtgctcacct tcctgtatca gattgtaggc aagggcaccc agcttttgtc    300
aaaactggaa aaggacgaca ctgtggaatt acagggcccg tacggcaagg gcttcccgga    360
tgtggacgcc gacctggtgg tggtgggcgg cggcattggt gtcgcgcccc tgtactatgt    420
gtgccgcgac ttcaagaaaa aacacccgga ccgcagcctg cgtgtttacc tgggctaccg    480
cgacactgcc tactgtgtgg aggaatttga cgcagtggcc gatgaagtgg tcgtggatat    540
cggcggcatc atcacccacc gggtagaagc ccgttccggc gaggtattct ttacctgcgg    600
cccggaaatc atgatgaaga gcctgtgtga cattgtcccg gccgaaaacc cggtttacgt    660
gtcgctggag gcgcatatgg cctgcggcat cggcgcctgt ctgggctgca cctgcgagac    720
cagtgaaggc aataagaagg tctgtaagga cgggccagtg tttaccagag aggtggcagc    780
cctatga                                                              787
```

GENOMIC EDITING VECTOR FOR *EUBACTERIUM CALLANDERI*, METHOD FOR EDITING GENOME OF *EUBACTERIUM CALLANDERI* USING THE SAME, AND TRANSGENIC *EUBACTERIUM CALLANDERI* STRAINS USING THE SAME

INCORPORATION OF SEQUENCE LISTING

This application contains a sequence listing submitted in Computer Readable Form (CRF). The CFR file containing the sequence listing is entitled "2-PJK4684868-SeqListing.txt", which was created and modified on Sep. 1, 2023, and is 19,048 bytes in size. The information in the sequence listing is incorporated herein by reference in its entirety.

BACKGROUND OF THE INVENTION

Field of the Invention

The present invention relates to a genomic editing vector for the CRISPR/Cas9 system, specifically to a genomic editing vector for the CRISPR/Cas9 system that can be applied to *Eubacterium callanderi* strains.

Description of the Related Art

As environmental problems and energy depletion due to the use of petroleum-based compounds become increasingly serious, the world reduces carbon dioxide emissions to prevent global warming caused by the use of fossil fuels and expedites the development of various alternative energy sources in preparation for high oil prices.

Syngas that is a representative alternative energy source may be produced by reforming natural gas or gasifying solid raw materials such as coal, organic wastes, and biomass.

Such syngas has the following advantages as an alternative energy source.

First, since syngas can be converted from most hydrocarbons, risk of raw material exhaustion is low, price fluctuation is less than that of fossil fuels, and thus raw materials can be stably secured.

Second, in the case of syngas-based energy conversion, carbon dioxide is not emitted but is used. Therefore, there is little concern about environmental pollution caused by carbon dioxide generation.

Third, since main components of the syngas are hydrogen and carbon, the syngas can be converted into various high value-added products such as acetic acid, butyric acid, ethanol, and butanol. Therefore, the syngas has high utilization potential and is economical.

The syngas can be used through a biorefinery using microorganisms. Typically, anaerobic acetic acid-producing bacteria called acetogen are used. Acetogen fixes C1 gases such as carbon monoxide and carbon dioxide to acetyl-CoA through the Wood-Ljungdhal pathway and converts the microorganisms into organic acids such as acetic acid to obtain energy necessary for cell growth.

In particular, *Eubacterium callanderi*, which is one of the acetogen, has several advantages suitable for syngas fermentation and refinery.

The biggest advantage is that, while the growth of other acetogen strains is inhibited due to the toxicity of carbon monoxide, which is one of the main components of syngas, the growth of *Eubacterium callanderi* is not inhibited even in the presence of carbon monoxide.

The growth rate and gas consumption rate are fast compared to other acetogen strains, and as the whole genome analysis is completed, it is advantageous in that the strain improvement thereof is easy.

The syngas biorefinery using acetogen is directly affected by the growth rate and gas consumption rate of microorganisms, and thus there is a problem in that the syngas biorefinery has a relatively low reaction rate and production efficiency compared to the chemical biorefinery in the related art.

Therefore, it is essential to improve strains for improving the productivity of acetogen to increase the efficiency of the biorefinery and producing new high value products.

However, there was a problem in that, though the *Eubacterium callanderi* strains have essential advantages suitable for use in syngas refinery, such as carbon monoxide resistance as described above, due to the absence of a genome editing system that can be applied to and improve the strains, *Eubacterium callanderi* strains are not actively improved and utilized.

CITATION LIST

Patent Literature

Patent Literature 1: Korean Unexamined Patent Publication No. 10-2017-0076822

SUMMARY OF THE INVENTION

The technical problem to be achieved by the present invention is to provide a genomic editing vector for *Eubacterium callanderi* that can be applied to *Eubacterium callanderi* strains which are acetogen suitable for syngas biorefinery.

The technical problem to be achieved by the present invention is to provide a method for editing a genome of *Eubacterium callanderi* strains using the editing vector for *Eubacterium callanderi*.

The technical problem to be achieved by the present invention is to provide transgenic *Eubacterium callanderi* strains using the editing vector for *Eubacterium callanderi*.

The technical problem to be achieved by the present invention is not limited to the above technical problems, and other technical problems that are not described herein can be clearly understood by a person skilled in the art to which the invention pertains from the descriptions below.

In order to achieve the above technical problems, an embodiment of the present invention provides a genomic editing vector for *Eubacterium callanderi* for the CRISPR/Cas9 system.

According to an embodiment of the present invention, the genomic editing vector for *Eubacterium callanderi* may include a DNA sequence encoding a guide RNA (gRNA) of a cleavage target gene; a DNA sequence encoding a Cas9 protein; a $P_{rbo}$ promoter that is operably linked to the DNA sequence encoding a Cas9 protein; a replication starting point derived from *E. coli*; a replication starting point for *Eubacterium callanderi*; and a marker for selecting transgenic strains.

The cleavage target gene may include an endogenous gene of *Eubacterium callanderi* strains.

The DNA sequence encoding a Cas9 protein may include a Cas9 gene having the nucleic acid sequence represented by SEQ ID NO: 1.

The DNA sequence encoding a Cas9 protein may include a Cas9 nickase gene having the nucleic acid sequence represented by SEQ ID NO: 2.

The $P_{rbo}$ promoter may have the nucleic acid sequence represented by SEQ ID NO: 3.

The replication starting point derived from *E. coli* may include any one selected from the group consisting of CloDF-13, pBBR1, p15A, oriC, pSC101, and pMB1.

The replication starting point for *Eubacterium callanderi* may include pIP404 replicon.

The marker for selecting transgenic strains may include an antibiotic resistance gene, and the antibiotic resistance gene includes any one selected from the group consisting of ampicillin, erythromycin, chloramphenicol, thiamphenicol, and tetracycline resistance genes.

In order to achieve the above technical problem, another embodiment of the present invention provides a genomic editing vector for *Eubacterium callanderi* for the CRISPR/Cas9 system.

According to another embodiment of the present invention, the genomic editing vector for *Eubacterium callanderi* may further include a 5' homology arm which is linked to a 3' end of the DNA sequence encoding the guide RNA and that is hybridized upstream of the cleavage target gene; a donor DNA sequence which is linked to a 3' end of the 5' homology arm and is a gene for insertion; and a 3' homology arm that is linked to a 3' end of the donor DNA sequence and is hybridized downstream of the cleavage target gene to the genomic editing vector for *Eubacterium callanderi* according to the embodiment of the present invention.

The donor DNA sequence may include an exogenous gene of *Eubacterium callanderi* strains.

In order to achieve the above technical problem, still another embodiment of the present invention provides a method for editing a genome of *Eubacterium callanderi* strains.

According to the embodiment of the present invention, the method for editing a genome of *Eubacterium callanderi* strains may include a step of introducing the genomic editing vector for *Eubacterium callanderi* according to the embodiment of the present invention into *Eubacterium callanderi* strains to be transformed; a step of selecting a strain to which the vector is introduced; and a step of cultivating the selected strain to obtain a transgenic strain.

In order to achieve the above technical problem, still another embodiment of the present invention provides a transgenic *Eubacterium callanderi* strain.

The transgenic *Eubacterium callanderi* strain is transformed by introduction of the genomic editing vector for *Eubacterium callanderi* according to the embodiment of the present invention.

BRIEF DESCRIPTION OF THE DRAWINGS

FIG. 2 is a diagram showing a nucleic acid sequence of a Cas9 gene having the nucleic acid sequence represented by SEQ ID NO: 1;

FIG. 4 is a diagram showing a nucleic acid sequence of a Cas9 nickase gene having the nucleic acid sequence represented by SEQ ID NO: 2;

FIG. 6 is a diagram showing a nucleic acid sequence of a $P_{rbo}$ promoter having the nucleic acid sequence represented by SEQ ID NO: 3;

FIG. 7 is a diagram showing a nucleic acid sequence of pMB1 on having the nucleic acid sequence represented by SEQ ID NO: 4 which is a replication starting point derived from *E. coli*;

FIG. 8 is a diagram showing a nucleic acid sequence of pIP404 having the nucleic acid sequence represented by SEQ ID NO: 5 which is a replication starting point for *Eubacterium callanderi*;

FIG. 11 is a diagram showing a nucleic acid sequence of a guide RNA having the nucleic acid sequence represented by SEQ ID NO: 14;

FIG. 12 is a diagram showing a nucleic acid sequence of a 5' homology arm having the nucleic acid sequence represented by SEQ ID NO: 15;

FIG. 13 is a diagram showing a nucleic acid sequence of a 3' homology arm having the nucleic acid sequence represented by SEQ ID NO: 16;

DETAILED DESCRIPTION OF THE PREFERRED EMBODIMENTS

Figure 1:
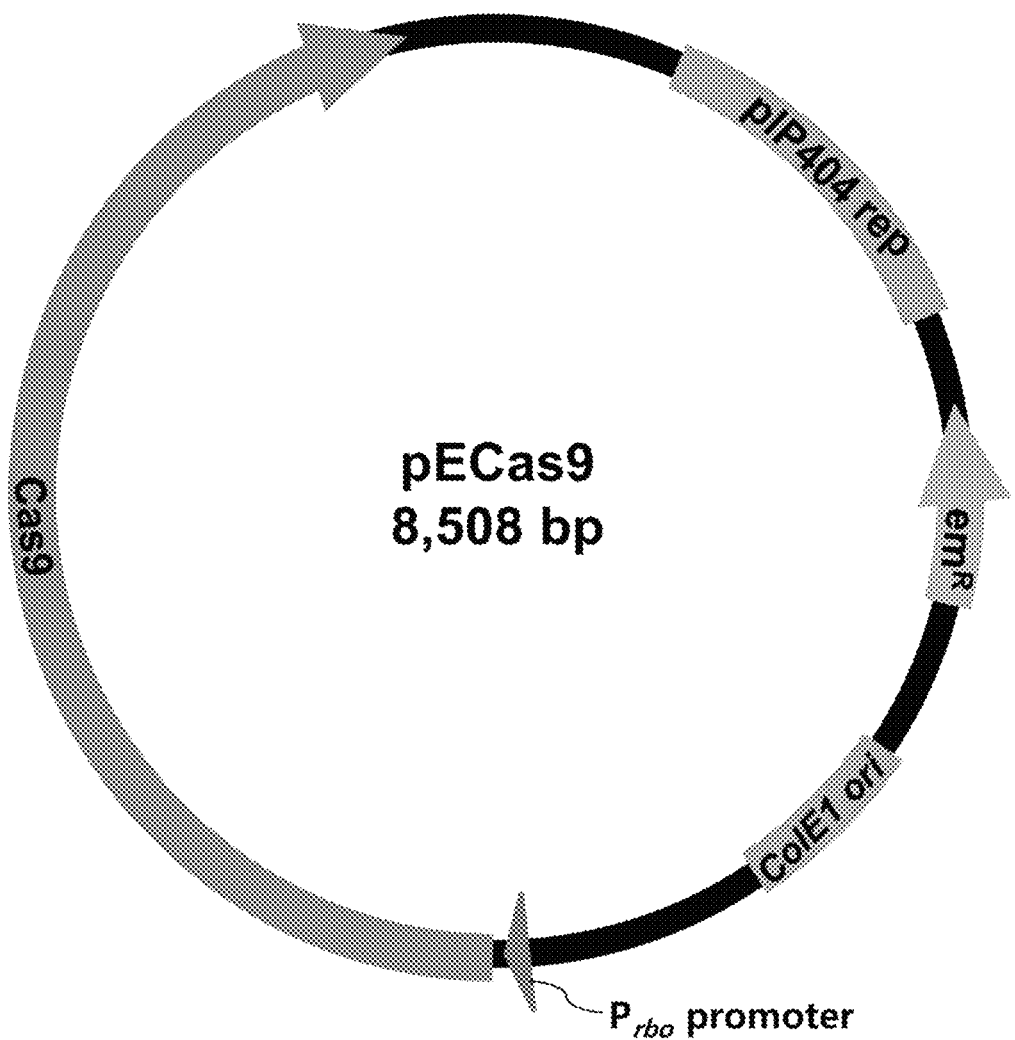
FIG. 1 is a diagram schematically showing a cleavage map of a genomic editing vector for *Eubacterium callanderi* according to an embodiment of the present invention.

Hereinafter, the present invention is described with reference to the accompanying drawings. However, the present invention may be embodied in several different forms, and thus is not limited to the embodiments described herein. In the drawings, in order to clearly explain the present invention, parts irrelevant to the description are omitted, and similar parts throughout the specification are denoted by similar reference numerals.

Throughout the specification, when it is described that a part is "linked (connected, in contact with, or coupled)" with another part, it includes not only a case of "being directly linked" but also a case of "being indirectly linked" with another member interposed therebetween. In addition, when it is described that a part "includes" a certain component, the description means that the part may further include other components, rather than excluding the other components, unless stated otherwise.

The terms used in the present specification are used only to describe specific embodiments and are not intended to limit the present invention. The singular expression includes the plural expression unless clearly stated otherwise in the context. In the present specification, terms such as "including" or "having" should be understood to be intended to designate the presence of features, numbers, steps, operations, components, parts, or combinations thereof described in the specification, but not to be intended to exclude in advance the presence or addition of one or more features, numbers, steps, operations, components, parts, or combinations thereof.

Hereinafter, embodiments of the present invention are described in detail with reference to the accompanying drawings.

A genomic editing vector for *Eubacterium callanderi* according to an embodiment of the present invention is described.

The genomic editing vector for *Eubacterium callanderi* can include a DNA sequence encoding a guide RNA (gRNA) of a cleavage target gene; a DNA sequence encoding a Cas9 protein; a $P_{rbo}$ promoter that is operably linked to the DNA sequence encoding a Cas9 protein; a replication starting point derived from *E. coli*; a replication starting point for *Eubacterium callanderi*; and a marker for selecting transgenic strains.

Though *Eubacterium callanderi* strains that are subjected to genome editing and become targets to be improved thereby have various advantages suitable for syngas fermentation and refinery, due to the absence of a genome editing system that can be applied for the improvement of the strains, *Eubacterium callanderi* strains are not actively improved and utilized.

The present inventors have conceived a genomic editing vector for *Eubacterium callanderi* for the CRISPR/Cas9 system that can be introduced into *Eubacterium callanderi* strain by combining components confirmed to be stably replicated when being introduced into other existing *Eubacterium* strains.

Therefore, the genomic editing vector for *Eubacterium callanderi* according to the embodiment of the present invention is stably applicable to *Eubacterium callanderi* strains compared to a genomic editing vector for the CRISPR/Cas9 system that cannot be applied to *Eubacterium callanderi* strains in the related art.

The cleavage target gene includes an endogenous gene of *Eubacterium callanderi* strains.

The term "endogeny" or "endogeneity" used in the present invention refers to an action or a substance originating from the inside in a broad sense and refers to a substance derived from the inside of an organism, a tissue or a cell in biology.

Therefore, the term "endogenous gene" used in the present invention refers to a gene derived from the inside of a specific strain and specifically refers to a gene to be a target of cleavage in *Eubacterium callanderi* strains in the present invention.

The guide RNA transcribed from the DNA sequence encoding a guide RNA (gRNA) of the cleavage target gene can include a target specific crRNA sequence and tracrRNA complementarily coupled to a nucleic acid sequence of the cleavage target gene. Therefore, the cleavage target gene coupled to the guide RNA is cleaved by the Cas9 enzyme, and the cleaved gene is restored by non-homologous end joining or homologous recombination. Therefore, the corresponding gene can be knocked out due to the above genetic modification so that the corresponding gene can no longer perform a normal function.

The DNA sequence encoding the Cas9 may be the Cas9 gene having the nucleic acid sequence represented by SEQ ID NO: 1.

The Cas9 gene having the nucleic acid sequence represented by SEQ ID NO: 1 is derived from pCas9 and may be derived from *Streptococcus pyogenes* or *Streptococcus thermophilus*.

The DNA sequence encoding the Cas9 may be a Cas9 nickase gene having the nucleic acid sequence represented by SEQ ID NO: 2.

At this point, the Cas9 nickase gene having the nucleic acid sequence represented by SEQ ID NO: 2 is derived from pNICKClos 1.0 and may be obtained by substituting the tenth amino acid of the Cas9 protein expressed from the Cas9 gene having the nucleic acid sequence represented by SEQ ID NO: 1 into alanine.

At this point, the Cas9 nickase may not cause double-stranded deletion but cause single-stranded deletion.

The $P_{rbo}$ promoter may include a nucleic acid sequence that is searched from a genome sequence of *Eubacterium limosum* strains belonging to the same genus as *Eubacterium callanderi* strains of the present invention and that matches by 90% or more with a promoter present at the upper end of a gene having a high average expression value of transcripts in the *Eubacterium limosum* strains.

More specifically, the $P_{rbo}$ promoter may have the nucleic acid sequence represented by SEQ ID NO: 3.

The replication starting point derived from *E. coli* may be any one selected from the group consisting of CloDF-13, pBBR1, p15A, oriC, pSC101, and pMB1.

The replication starting point derived from *E. coli* is preferably pMB1 ori.

At this point, the pMB1 on may be derived from the pJIR418 vector (Sloan J et al., Elsevier, 27:3, 1992) confirmed to be stably replicated when being introduced into existing *Eubacterium* strains.

More specifically, the pMB1 on may have the nucleic acid sequence represented by SEQ ID NO: 4.

The replication starting point for *Eubacterium callanderi* may be pIP404 replicon.

At this point, the pIP404 replicon may be derived from the pJIR418 vector (Sloan J et al., Elsevier, 27:3, 1992) confirmed to be stably replicated when being introduced into existing *Eubacterium* strains.

More specifically, the pIP404 replicon may have the nucleic acid sequence represented by SEQ ID NO: 5.

The marker for selecting transgenic strains may include an antibiotic resistance gene, and the antibiotic resistance gene may be any one selected from the group consisting of ampicillin, erythromycin, chloramphenicol, thiamphenicol, and tetracycline resistance genes, but the present embodiment is not limited thereto, and any antibiotic resistance gene in the art can be used without limitation.

FIG. 1 is a diagram schematically showing a cleavage map of the genomic editing vector for *Eubacterium callanderi* according to the embodiment of the present invention, in which the DNA sequence encoding the Cas9 is a Cas9 gene having the nucleic acid sequence represented by SEQ ID NO: 1.

FIG. 2 is a diagram showing a nucleic acid sequence of the Cas9 gene having the nucleic acid sequence represented by SEQ ID NO: 1.

Figure 3:
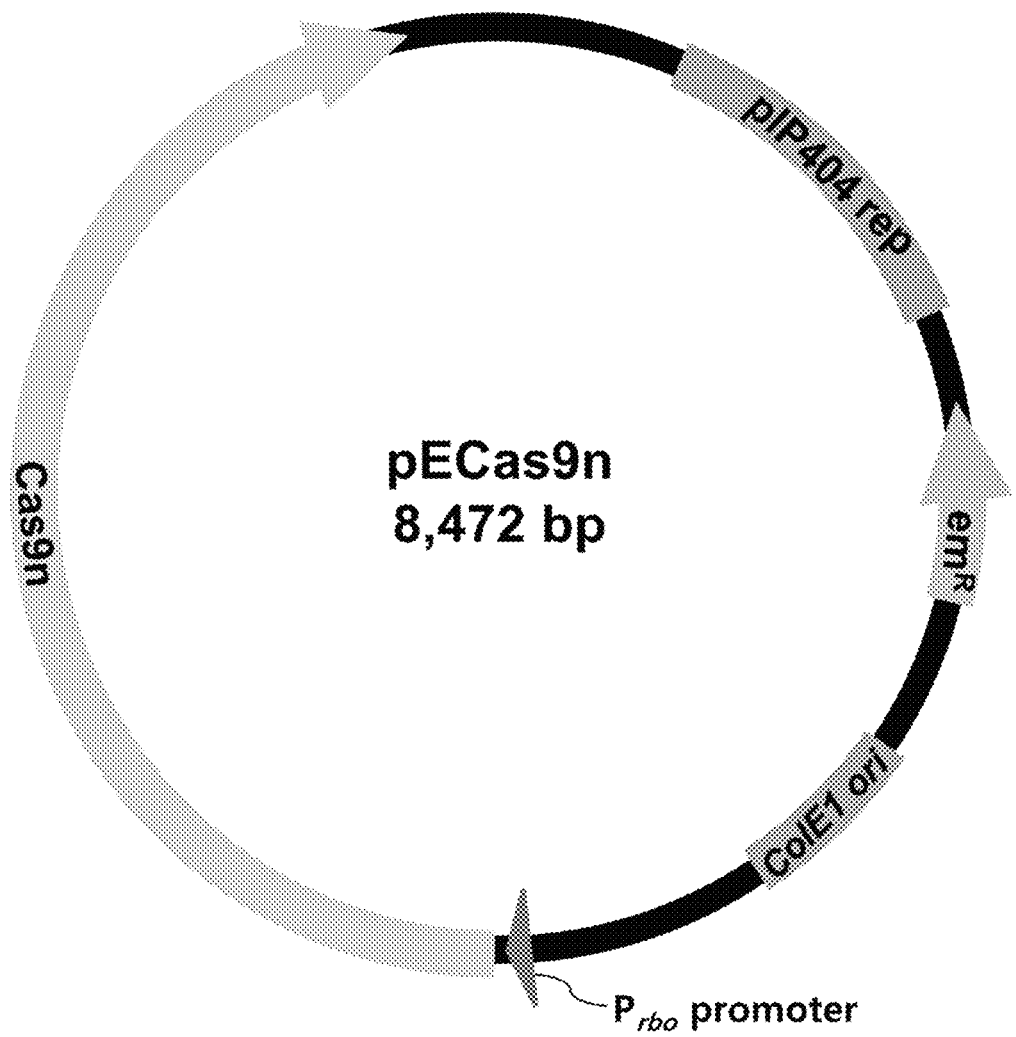
FIG. 3 is a diagram schematically showing a cleavage map of a genomic editing vector for *Eubacterium callanderi* according to another embodiment of the present invention.

FIG. 3 is a diagram schematically showing a cleavage map of the genomic editing vector for *Eubacterium callanderi* according to another embodiment of the present invention, in which the DNA sequence encoding the Cas9 is the Cas9 nickase gene having the nucleic acid sequence represented by SEQ ID NO: 2.

Figure 4:
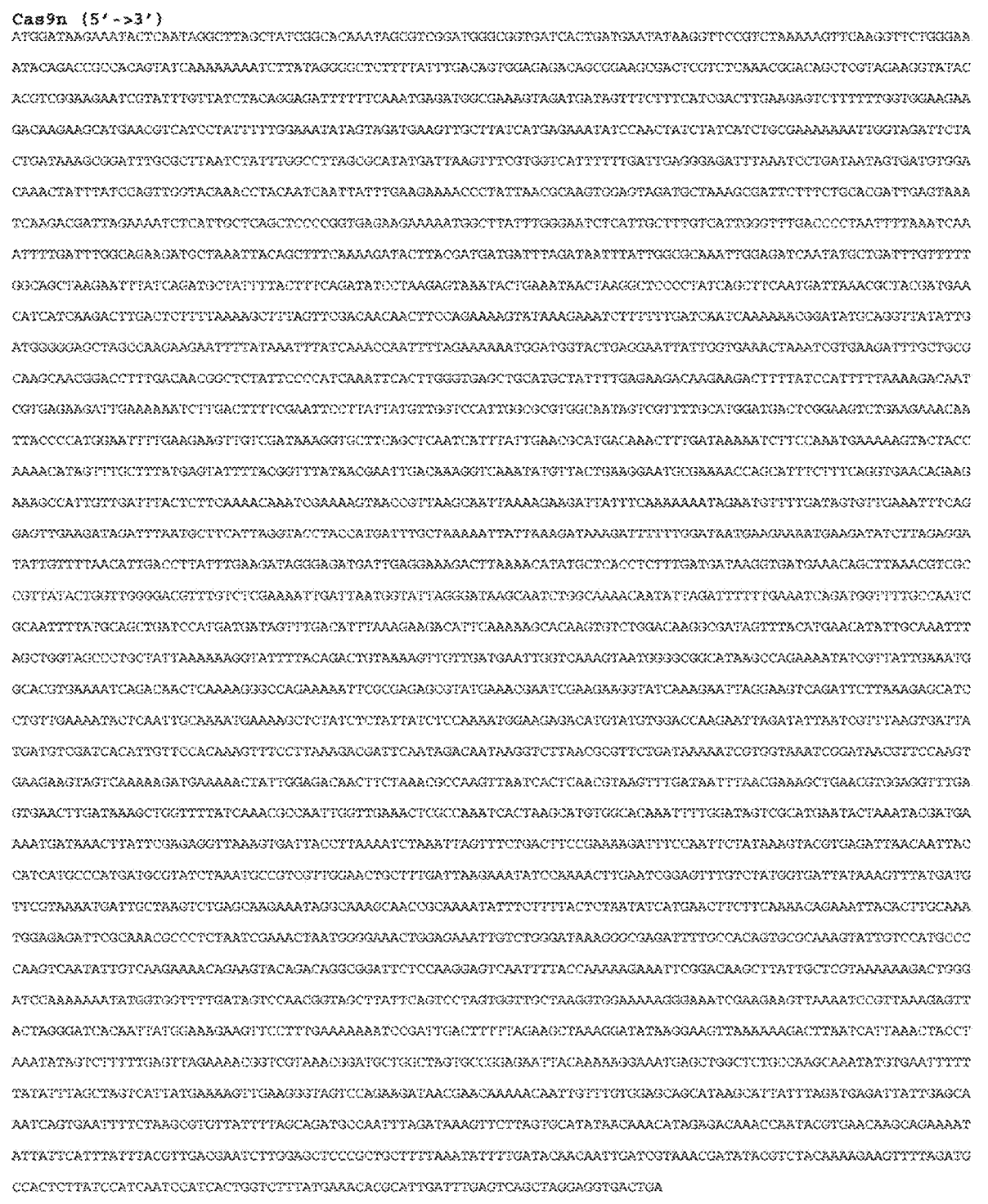

FIG. 4 is a diagram illustrating the nucleic acid sequence of the Cas9 nickase gene having the nucleic acid sequence represented by SEQ ID NO: 2.

With reference to FIGS. 1 to 4, a schematic cleavage map of the genomic editing vector for *Eubacterium callanderi* according to the embodiment of the present invention can be confirmed.

According to the embodiment of the present invention, the characterizations of the above configuration have an effect of providing the genomic editing vector for the CRISPR/Cas9 genomic editing system that enables the knockout through the cleavage of a specific target gene of *Eubacterium callanderi*.

The genomic editing vector for *Eubacterium callanderi* according to another embodiment of the present invention is described.

In addition to the DNA sequence encoding a guide RNA (gRNA) of the cleavage target gene; the DNA sequence encoding a Cas9 protein; the $P_{rbo}$ promoter that is operably linked to the DNA sequence encoding a Cas9 protein; the replication starting point derived from *E. coli*; the replication starting point for *Eubacterium callanderi*; and the marker for selecting transgenic strains, the genomic editing vector for *Eubacterium callanderi* may further include a 5' homology arm that is linked to the 3' end of the DNA sequence encoding the guide RNA and is hybridized upstream of the cleavage target gene; a donor DNA sequence that is linked to the 3' end of the 5' homology arm and is a gene for insertion; and a 3' homology arm that is linked to the 3' end of the donor DNA sequence and is hybridized downstream of the cleavage target gene.

At this point, the donor DNA sequence may further include an exogenous gene of *Eubacterium callanderi* strains.

The term "exogeny" or "exogeneity" used in the present invention refers to an action or a substance originating from the outside in a broad sense and refers to a substance derived from the outside of an organism, a tissue, or a cell in biology.

Therefore, the term "exogenous gene" used in the present invention refers to a gene that is derived from the outside and that does not exist in a specific strain. The gene derived from the outside may refer to a gene of a completely novel nucleic acid sequence, but may also include a gene in the form in which the sequence of a gene already existing in a specific strain is partially modified.

According to the characterizations of the above configuration, the guide RNA transcribed from the DNA sequence encoding the guide RNA (gRNA) is complementarily coupled to the cleavage target gene, the cleavage target gene coupled to the guide RNA is cleaved by the Cas9 enzyme, the 5' homology arm is hybridized upstream of the cleavage target gene, and the 3' homology arm is hybridized downstream of the cleavage target gene, and thus the donor DNA sequence that is the gene for insertion therebetween is inserted to the cleaved part. According to the above system, the exogenous gene can be introduced into the *Eubacterium callanderi* strain and expressed.

According to the embodiment of the present invention, the characterizations of the above configuration have an effect of providing a genomic editing vector for the CRISPR/Cas9 genomic editing system that enables the strain improvement by inserting a specific target gene into the *Eubacterium callanderi* strain.

A method for editing a genome of *Eubacterium callanderi* strains according to another embodiment of the present invention is described.

The method for editing a genome of *Eubacterium callanderi* strains may include a step of introducing a genomic editing vector for *Eubacterium callanderi* according to the embodiment of the present invention into *Eubacterium callanderi* strains to be transformed; a step of selecting strains to which the vector is introduced; and a step of cultivating selected strains to obtain transgenic strains.

According to the embodiment of the present invention, the characterizations of the above configuration have an effect of being capable of providing a method for editing a genome of *Eubacterium callanderi* strains that have various advantages suitable for syngas fermentation and refinery.

The transgenic *Eubacterium callanderi* strains according to another embodiment of the present invention are described.

The transgenic *Eubacterium callanderi* strain may be transgenic through the introduction of the genomic editing vector for *Eubacterium callanderi* according to the embodiment of the present invention.

According to the embodiment of the present invention, the characterization of the above configuration can provide transgenic *Eubacterium callanderi* strains that are improved to have improved performance in the syngas fermentation and refinery.

Hereinafter, the present invention is more specifically described through manufacturing examples, comparative examples, and experimental examples. However, the present invention is not limited to the following manufacturing examples and experimental examples.

<Manufacturing Example 1> Manufacturing of pECas9 Vector

A genomic editing vector for *Eubacterium callanderi* according to the embodiment of the present invention was manufactured.

Figure 5:
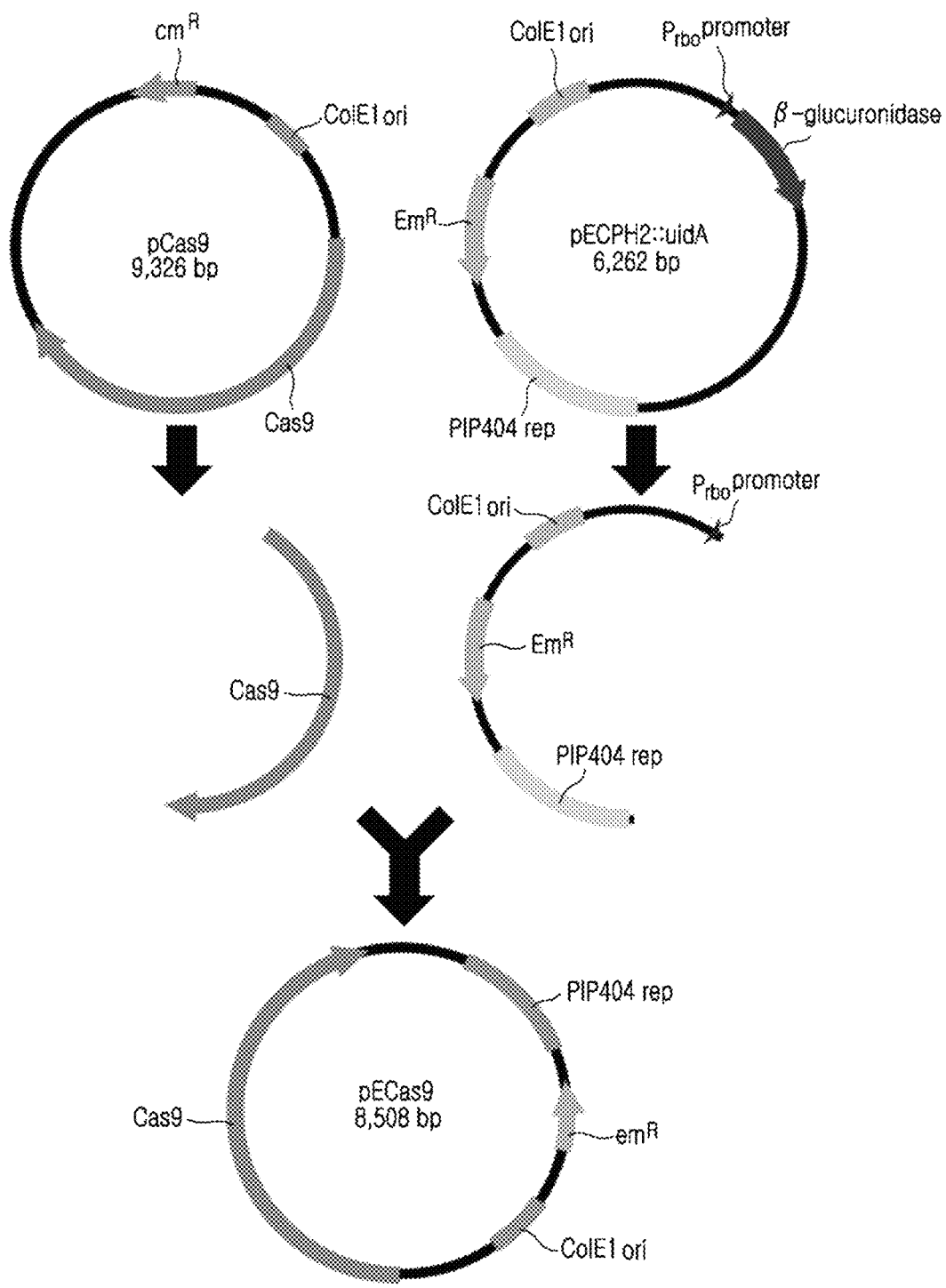
FIG. 5 is a schematic view schematically showing a process of constructing the pECas9 vector that is a genomic editing vector for *Eubacterium callanderi* according to the embodiment of the present invention.

FIG. 5 is a schematic view schematically showing a process of constructing the pECas9 vector that is a genomic editing vector for *Eubacterium callanderi* according to the embodiment of the present invention.

FIG. 6 is a diagram showing a nucleic acid sequence of a $P_{rbo}$ promoter having the nucleic acid sequence represented by SEQ ID NO: 3.

FIG. 7 is a diagram showing a nucleic acid sequence of pMB1 on having the nucleic acid sequence represented by SEQ ID NO: 4 which is a replication starting point derived from *E. coli*.

FIG. 8 is a diagram showing a nucleic acid sequence of pIP404 having the nucleic acid sequence represented by SEQ ID NO: 5 which is a replication starting point for *Eubacterium callanderi*.

The process of manufacturing the genomic editing vector for *Eubacterium callanderi* according to the embodiment of the present invention is described with reference to FIGS. 5 to 8.

In order to manufacture the genomic editing vector for *Eubacterium callanderi* according to the embodiment of the present invention, first, a back bone vector was prepared. The back bone vector included pMB1 on having the nucleic acid sequence represented by SEQ ID NO: 4 which is the replication starting point derived from *E. coli*, pIP404 having the nucleic acid sequence represented by SEQ ID NO: 5 which is the replication starting point for *Eubacterium callanderi*, and an Erythromycin resistant gene ($em^R$) to be used as a marker for selecting transgenic strains. For this, the pECPH2::uidA vector disclosed in Korean Patent No. 10-2073308 was amplified by using a forward primer FW_pJBB having the nucleic acid sequence represented by SEQ ID NO: 6 and a reverse primer RV_pJBB having the nucleic acid sequence represented by SEQ ID NO: 7.

Through the above process, the back bone vector for manufacturing the genomic editing vector for *Eubacterium callanderi* according to the present invention was prepared.

A $P_{rbo}$ promoter having the nucleic acid sequence represented by SEQ ID NO: 3 which is to be inserted into the back bone vector was prepared. In the same manner, the $P_{rbo}$ promoter amplified the pECPH2::uidA vector by using a forward primer FW_Native H3 having the nucleic acid sequence represented by SEQ ID NO: 8 and the reverse primer RV_Native H3 having the nucleic acid sequence represented by SEQ ID NO: 9.

According to the above process, the $P_{rbo}$ promoter having the nucleic acid sequence represented by SEQ ID NO: 3 for manufacturing the genomic editing vector for *Eubacterium callanderi* according to the present invention was prepared.

The Cas9 gene having the nucleic acid sequence of SEQ ID NO: 1 to be inserted into the back bone vector was prepared. The Cas9 gene having the nucleic acid sequence represented by SEQ ID NO: 1 amplified a pCas9 vector (RNA-guided editing of bacterial genomes using CRISPR-Cas systems. Jiang W, Bikard D, CoxD, Zhang F, Marraffini L A. Nat Biotechnol. 2013 Jan. 29. doi: 10. 1038/nbt.2508. 10.1038/nbt.2508PubMed23360965) by using a forward primer FW_Cas9 having the nucleic acid sequence represented by SEQ ID NO: 10 and a reverse primer RV_Cas9 having the nucleic acid sequence represented by SEQ ID NO: 11.

According to the above process, the Cas9 gene having the nucleic acid sequence represented by SEQ ID NO: 1 for manufacturing the genomic editing vector for *Eubacterium callanderi* of the present invention was prepared.

The genomic editing vector for *Eubacterium callanderi* according to the embodiment of the present invention was manufactured by performing combination of the back bone vector prepared as above, the $P_{rbo}$ promoter having the nucleic acid sequence represented by SEQ ID NO: 3, and the Cas9 gene having the nucleic acid sequence represented by SEQ ID NO: 1 by using the Gibson assembly master mix (NEB) and was named as the pECas9 vector.

<Manufacturing Example 2> Manufacturing of pECas9n Vector

The pECas9n vector was manufactured in the same process as in Manufacturing example 1 except that the Cas9 nickase gene having the nucleic acid sequence represented by SEQ ID NO: 2 was used instead of the Cas9 gene having the nucleic acid sequence represented by SEQ ID NO: 1 in Manufacturing example 1.

Figure 9:
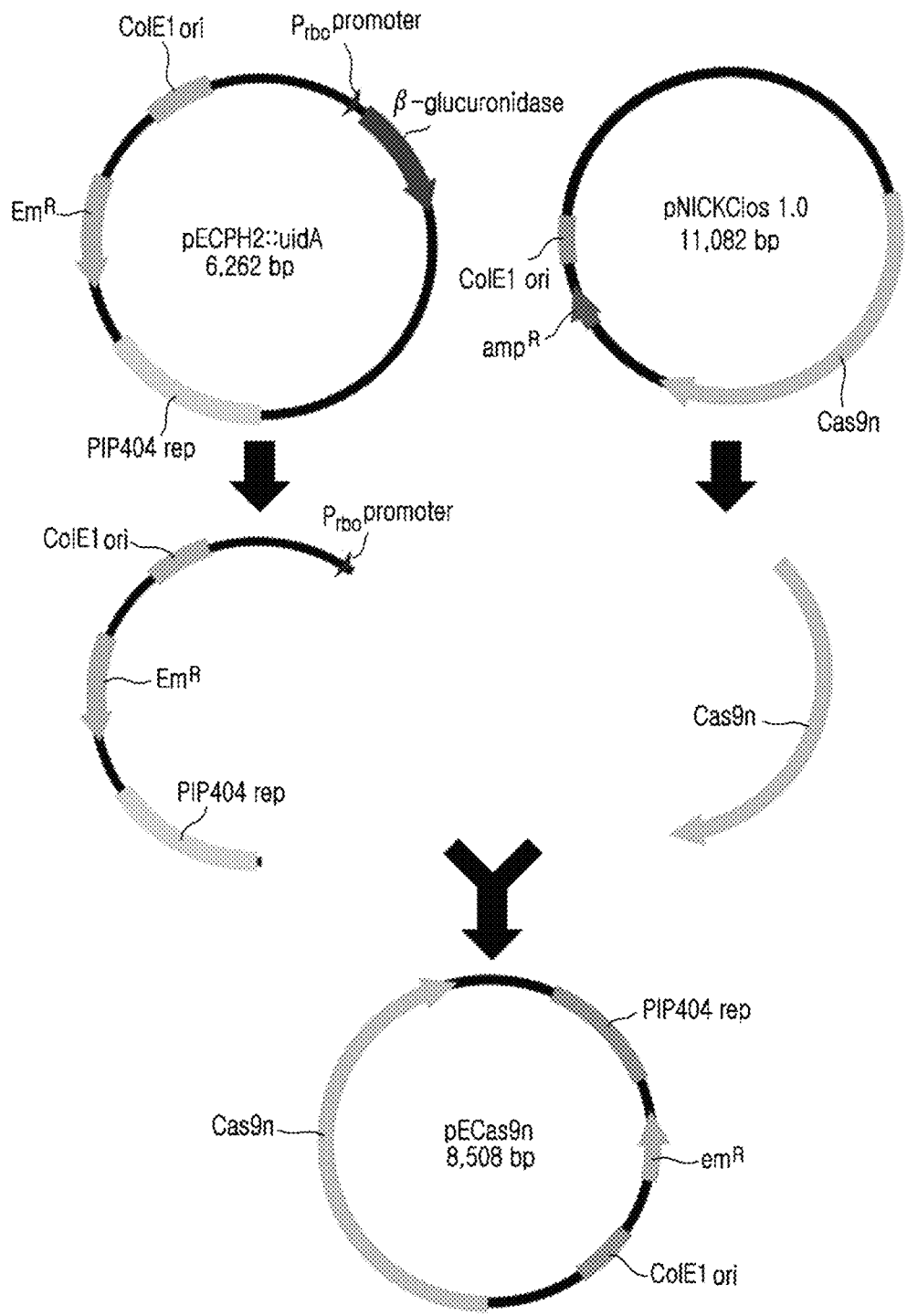
FIG. 9 is a schematic view schematically showing a construction process of the pECas9n vector which is a genomic editing vector for *Eubacterium callanderi* according to the embodiment of the present invention.

FIG. 9 is a schematic view schematically showing a construction process of the pECas9n vector which is a genomic editing vector for *Eubacterium callanderi* according to the embodiment of the present invention.

The Cas9 nickase gene having the nucleic acid sequence represented by SEQ ID NO: 2 amplified a pNICKclos1.0 vector (ref. CRISPR-based genome editing and expression control systems in *Clostridium acetobutylicum* and *Clostridium beijerinckii*. LiQ, Chen J, Minton N P, Zhang Y, Wen Z, Liu J, Yang H, Zeng Z, Ren X, Yang J, Gu Y, Jiang W, Jiang Y, Yang S. Biotechnol J. 2016 May 23. doi: 10. 1002/biot. 201600053.10.1002/biot.201600053 PubMed 27213844) by using a forward primer FW_Cas9n having the nucleic acid sequence represented by SEQ ID NO: 12 and a reverse primer RV_Cas9n having the nucleic acid sequence represented by SEQ ID NO: 13.

The genomic editing vector for *Eubacterium callanderi* according to the embodiment of the present invention was manufactured by combining the Cas9 nickase gene having the nucleic acid sequence represented by SEQ ID NO: 2 which was prepared by the same process as in Manufacturing example 1 and was named as the pECas9n vector.

Table 1 is a table showing nucleic acid sequences of the primers used in Manufacturing examples 1 and 2.

TABLE 1

| Primer | SEQ ID NO. | Nucleic acid sequence |
|---|---|---|
| FW_pJBB | SEQ ID NO: 6 | 5'-GTT ACA TCG GGT TAC ATC GAA CTG GAT CTC AAC AGC G-3' |
| RV_pJBB | SEQ ID NO: 7 | 5'-GAC TAG TCA GAA TCA GGG GAT AAC GCA GGA-3' |
| FW_Native H3 | SEQ ID NO: 8 | 5'-CTC ACA TGT TCT TTC CTG CGT TAT CCC CTG ATT CTG ACT AGT CTG CAC CAT CAA TGA CAT CAC ACA GCA TAA CG-3' |
| RV_Native H3 | SEQ ID NO: 9 | 5'-AGC CTA TTG AGT ATT TCT TAT CCA TAA TAA AGA CCT CCT ATA GTC CAA ATA TAA TTT TGA GCA GTC CGT G-3' |
| FW_Cas9 | SEQ ID NO: 10 | 5'-CAC GGA CTG CTC AAA ATT ATA TTT GGA CTA TAG GAG GTC TTT ATT ATG GAT AAG AAA TAC TCA ATA GGC TTA GAT ATC GGC ACA AAT AGC G-3' |
| RV_Cas9 | SEQ ID NO: 11 | 5'-ATC TTA CCG CTG TTG AGA TCC AGT TCG ATG TAA CCC GAT GTA ACC CCA CTA TTT GTC TCA GCT AGA CTT CAG TC-3' |
| FW_Cas9n | SEQ ID NO: 12 | 5'-CAC GGA CTG CTC AAA ATT ATA TTT GGA CTA TAG GAG GTC TTT ATT ATG GAT AAG AAA TAC TCA ATA GGC TTA GCT ATC GGC ACA AAT AGC-3' |
| RV_Cas9n | SEQ ID NO: 13 | 5'-ATC TTA CCG CTG TTG AGA TCC AGT TCG ATG TAA CCC GAT GTA ACC CCG ATT AAG TTG GGT AAC GCC-3' |

<Embodiment 1> Manufacturing of Vector for Knockout of pyrF Gene

In order to confirm whether the CRISPR/Cas9 system using the genomic editing vector for *Eubacterium callanderi* manufactured in Manufacturing example 1 operated, the genomic editing vector for knockout of the pyrF gene of *Eubacterium callanderi* strains was manufactured.

Figure 10:
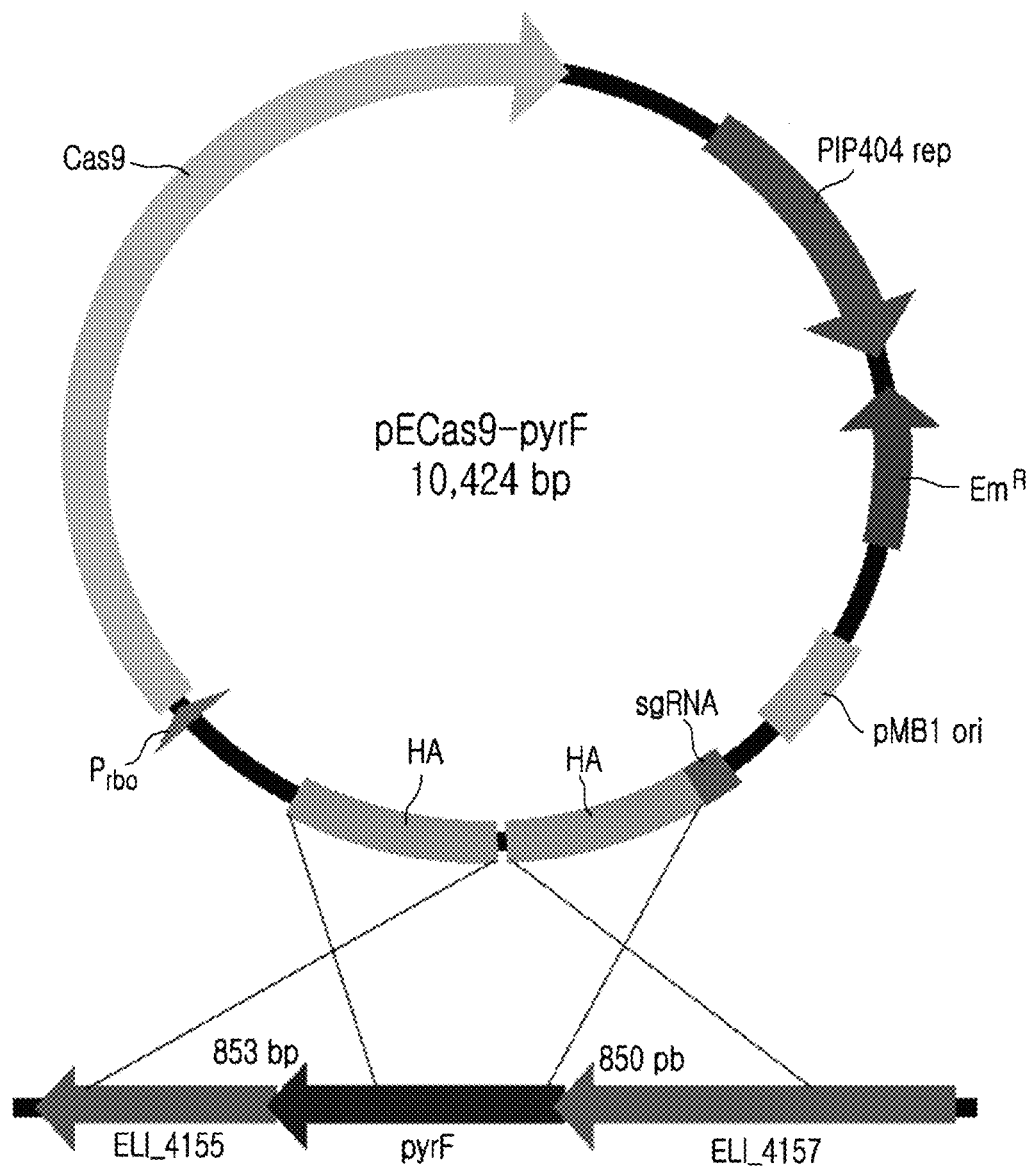
FIG. 10 is a diagram schematically showing a cleavage map of a genomic editing vector for knockout of the pyrF gene of *Eubacterium callanderi* strains according to the embodiment of the present invention.

FIG. 10 is a diagram schematically showing a cleavage map of a genomic editing vector for knockout of the pyrF gene of *Eubacterium callanderi* strains according to the embodiment of the present invention.

FIG. 11 is a diagram showing a nucleic acid sequence of a guide RNA having the nucleic acid sequence represented by SEQ ID NO: 14.

FIG. 12 is a diagram showing a nucleic acid sequence of a 5' homology arm having the nucleic acid sequence represented by SEQ ID NO: 15.

FIG. 13 is a diagram showing a nucleic acid sequence of a 3' homology arm having the nucleic acid sequence represented by SEQ ID NO: 16.

In a method for manufacturing a genomic editing vector for knockout of the pyrF gene of *Eubacterium callanderi* strains according to the embodiment of the present invention described with reference to FIGS. 10 to 13, the genomic editing vector pECas9 vector of Manufacturing example 1 and the DNA fragment for the pyrF knockout were treated with restriction enzyme SpeI for three hours, and then were linked to each other by using T4 ligase. At this point, the DNA fragment for pyrF knockout includes a DNA sequence encoding the guide RNA having the nucleic acid sequence represented by SEQ ID NO: 14, the 5' homology arm having the nucleic acid sequence represented by SEQ ID NO: 15, and the 3' homology arm having the nucleic acid sequence represented by SEQ ID NO: 16.

The vector for pyrF gene knockout manufactured as above is named as pECas9-pyrF.

<Embodiment 2> Manufacturing of PyrF Deletion *Eubacterium callanderi* Strain In order to confirm whether the CRISPR/Cas9 system using the pECas9-pyrF vector manufactured in Embodiment 1 operates, the pECas9-pyrF vector manufactured in Embodiment 1 was introduced into the *Eubacterium callanderi* strains to manufacture a pyrF deletion *Eubacterium callanderi* strain (hereinafter, referred to as a ΔpyrF strain).

<Experimental Example 1> Experiment for Confirming pyrF Gene Knockout of ΔpvrF Strain In order to confirm whether the *Eubacterium callanderi* strains of the CRISPR/Cas9 system using the genomic editing vector according to the embodiment of the present invention operates, an experiment for confirming the actual pyrF gene knockout of the ΔpyrF strain manufactured in Embodiment 2 was performed.

Figure 14:
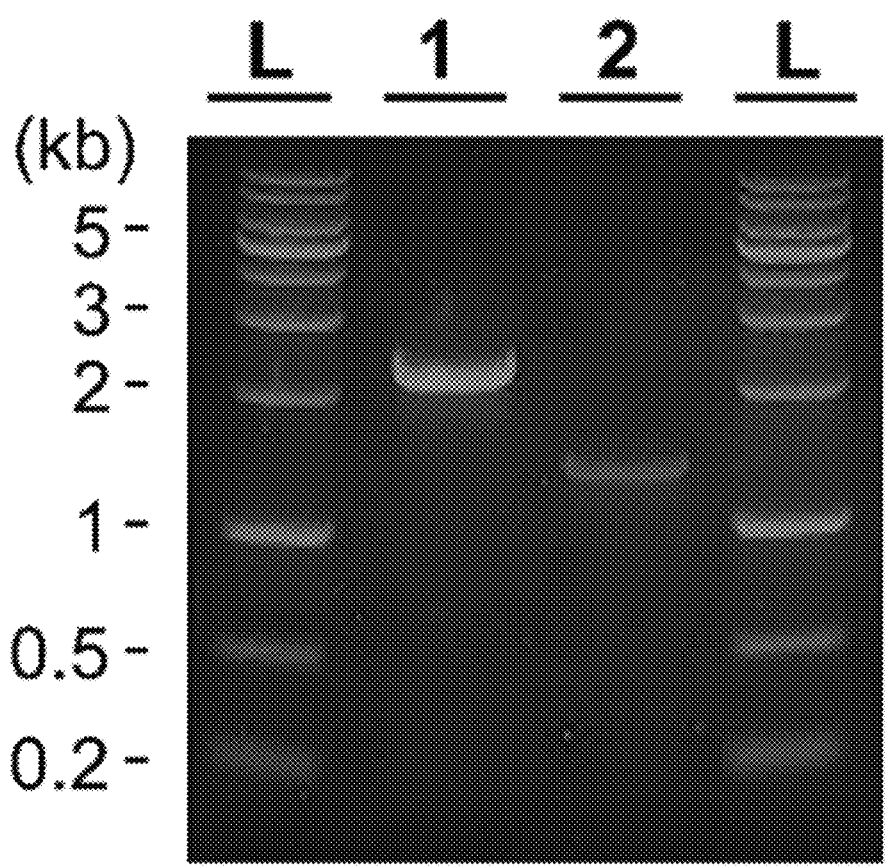
FIG. 14 is a photograph showing PCR amplification and electrophoresis results of a ΔpyrF strain according to the embodiment of the present invention and a wild-type *Eubacterium callanderi* strain.

FIG. 14 is a photograph showing PCR amplification and electrophoresis results of the ΔpyrF strain according to the embodiment of the present invention and a wild-type *Eubacterium callanderi* strain.

With reference to FIG. 14, since a fragment of 2.2 kb in case of 1 which is the PCR result of the wild-type strain and a fragment of 1.6 kb in case of 2 which is the PCR result of the ΔpyrF strain were obtained, it can be confirmed that pyrF was deleted from the genome.

It is known that in the *Eubacterium callanderi* strain, when a deletion occurs in the pyrF gene, which is involved in the uracil biosynthetic pathway, the ΔpyrF strain becomes a uracil auxotroph.

Figure 15:
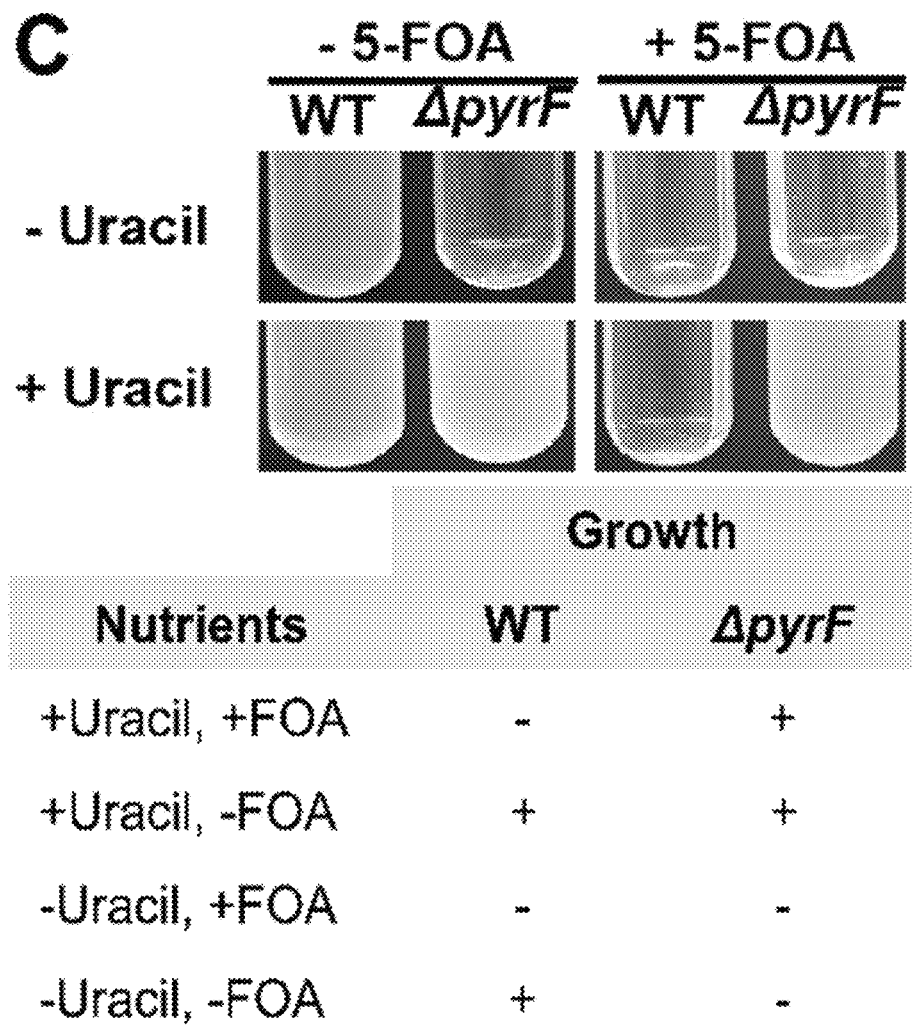
FIG. 15 is a table showing the growth confirmation of the ΔpyrF strain according to the embodiment of the present invention and the wild-type *Eubacterium callanderi* strain depending on the presence of uracil and 5-fluoroorotic acid.

FIG. 15 is a table showing the growth confirmation of the ΔpyrF strain according to the embodiment of the present invention and the wild-type *Eubacterium callanderi* strain depending on the presence of uracil and 5-fluoroorotic acid.

With reference to FIG. 15, it is confirmed that the wild-type strain was able to be grown in the −Uracil environment in which uracil did not exist, but was not resistant to 5-fluoroorotic acid, and thus was not grown in the +FOA environment. The ΔpyrF strain was uracil auxotroph, and thus was not able to be grown in the −Uracil environment in which uracil did not exist, and was grown only in the +Uracil environment. Therefore, it is confirmed that the pyrF gene of the ΔpyrF strain was effectively knocked out.

According to an embodiment of the present invention, there is an effect of being capable of providing a genomic editing vector for *Eubacterium callanderi* that can be applied to *Eubacterium callanderi* strains that are acetogen suitable for syngas biorefinery.

According to the embodiment of the present invention, there is an effect of being capable of providing a method for editing a genome of *Eubacterium callanderi* strains using the editing vector for *Eubacterium callanderi*.

According to the embodiment of the present invention, there is an effect of being capable of providing transgenic *Eubacterium callanderi* strains using the editing vector for *Eubacterium callanderi*.

Effects of the present invention are not limited to the above effects, and it should be understood to include all effects that can be inferred from the configuration of the invention described in the detailed description or claims of the present invention.

The above description of the present invention is merely an example, and it should be understood that a person skilled in the art to which the invention pertains can easily modify the present invention into other specific forms without changing the technical spirit or essential features thereof. Therefore, it should be understood that the embodiments described above are illustrative in all respects but not restrictive. For example, each component described as a single type may be implemented in a dispersed form, and in the same manner, components described as distributed may be implemented in a coupled form.

The scope of the present invention is indicated by the following claims, and all changes or modifications derived from the meaning and the scope of the claims and equivalents thereof should be construed as being included in the scope of the present invention.

What is claimed is:

1. A genomic editing vector for *Eubacterium callanderi*, comprising:

a DNA sequence encoding a guide RNA (gRNA) of a cleavage target gene;

a DNA sequence encoding a Cas9 protein;

a $P_{rbo}$ promoter that is operably linked to the DNA sequence encoding a Cas9 protein;

a replication starting point derived from *E. coli;* a replication starting point for *Eubacterium callanderi*; and a marker for selecting transgenic strains.

2. The genomic editing vector for *Eubacterium callanderi* according to claim 1, wherein the cleavage target gene includes an endogenous gene of *Eubacterium callanderi* strains.

3. The genomic editing vector for *Eubacterium callanderi* according to claim 1, wherein the DNA sequence encoding a Cas9 protein comprises the nucleic acid sequence of SEQ ID NO: 1.

4. The genomic editing vector for *Eubacterium callanderi* according to claim 1, wherein the DNA sequence encoding a Cas9 protein comprises the nucleic acid sequence of SEQ ID NO: 2.

5. The genomic editing vector for *Eubacterium callanderi* according to claim 1, wherein the $P_{rbo}$ promoter has the nucleic acid sequence represented by SEQ ID NO: 3.

6. The genomic editing vector for *Eubacterium callanderi* according to claim 1, wherein the replication starting point derived from *E. coli* includes any one selected from the group consisting of CloDF-13 ori, pBBR1 ori, p15A ori, oriC, pSC101 ori, and pMB1 ori.

7. The genomic editing vector for *Eubacterium callanderi* according to claim 1, wherein the replication starting point for *Eubacterium callanderi* is a pIP404 origin.

8. The genomic editing vector for *Eubacterium callanderi* according to claim 1, wherein the marker for selecting transgenic strains includes an antibiotic resistance gene, and the antibiotic resistance gene includes any one selected from the group consisting of ampicillin, erythromycin, chloramphenicol, thiamphenicol, and tetracycline resistance genes.

9. The genomic editing vector for *Eubacterium callanderi* according to claim 1, further comprising:

a 5' homology arm which is linked to a 3' end of the DNA sequence encoding the guide RNA and that is complementary to the region upstream of the cleavage target gene;

a donor DNA sequence which is linked to a 3' end of the 5' homology arm and is a gene for insertion; and a 3' homology arm that is linked to a 3' end of the donor DNA sequence and is complementary to the region downstream of the cleavage target gene.

10. The genomic editing vector for *Eubacterium callanderi* according to claim 9, wherein the gene for insertion includes an exogenous gene of *Eubacterium callanderi* strains.

11. A method for editing a genome of *Eubacterium callanderi* strains, the method comprising:

introducing the genomic editing vector for *Eubacterium callanderi* according to claim 1 into *Eubacterium callanderi* strains to be transformed;

selecting a strain having the genomic editing vector by using the marker of the vector; and cultivating the selected strain to obtain a transgenic strain.

12. A transgenic *Eubacterium callanderi* strain that is transformed by introduction of the genomic editing vector for *Eubacterium callanderi* according to claim 1.

* * * * *